US012502318B2

(12) United States Patent
Corneliusson et al.

(10) Patent No.: US 12,502,318 B2
(45) Date of Patent: Dec. 23, 2025

(54) REUSABLE OUTER SHELL FOR AN ABSORBENT INSERT

(71) Applicant: Essity Hygiene and Health Aktiebolag, Gothenburg (SE)

(72) Inventors: Helena Corneliusson, Gothenburg (SE); Cecilia Thelin, Gothenburg (SE); Mattias Johansson, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 281 days.

(21) Appl. No.: 18/263,781

(22) PCT Filed: Feb. 26, 2021

(86) PCT No.: PCT/EP2021/054847

§ 371 (c)(1),
(2) Date: Aug. 1, 2023

(87) PCT Pub. No.: WO2022/179697

PCT Pub. Date: Sep. 1, 2022

(65) Prior Publication Data

US 2024/0082074 A1 Mar. 14, 2024

(51) Int. Cl.
*A61F 13/505* (2006.01)
*A61F 13/76* (2006.01)

(52) U.S. Cl.
CPC .................................. *A61F 13/505* (2013.01)

(58) Field of Classification Search
CPC .......... A61F 13/15268; A61F 13/49003; A61F 13/49004; A61F 13/505; A61F 13/66;
(Continued)

(56) References Cited

U.S. PATENT DOCUMENTS 5,069,672 A * 12/1991 Wippler .................. A61F 13/76 604/398
6,254,583 B1 * 7/2001 Coates .............. A61F 13/49004 604/394
(Continued)

FOREIGN PATENT DOCUMENTS

EP 2810629 A1 12/2014
JP 2011050525 A 3/2011
(Continued)

OTHER PUBLICATIONS

International Search Report (PCT/ISA/210) and Written Opinion (PCT/ISA/237) mailed on Nov. 23, 2021, by the European Patent Office as the International Searching Authority for International Application No. PCT/EP2021/054847. (10 pages).
(Continued)

*Primary Examiner* — Catharine L Anderson
(74) *Attorney, Agent, or Firm* — BUCHANAN INGERSOLL & ROONEY PC

(57) ABSTRACT

A reusable outer shell (1) for a disposable absorbent insert (2) the outer shell (1) including an inner surface (3) intended to face the absorbent insert (2) and an outer surface (4) being opposite to the inner surface (3), the outer shell (1) including a front pocket (8) and a rear pocket (9), the front pocket being adapted to receive a front portion (**2*a*) of the absorbent insert (2) and the rear pocket being adapted to receive a rear portion (2*b*) of the absorbent insert (2**), the front pocket having a front pocket length ($l_{fp}$), and the rear pocket having a rear pocket length ($l_{rp}$), and wherein the rear pocket length ($l_{rp}$) is greater than the front pocket length ($l_{fp}$).

16 Claims, 3 Drawing Sheets

(58) Field of Classification Search
CPC .......... A61F 13/68; A61F 13/70; A61F 13/74; A61F 13/76; A61F 2013/15276
See application file for complete search history.

(56) References Cited

U.S. PATENT DOCUMENTS

| | | | | |
|---|---|---|---|---|
| 8,696,643 | B2 * | 4/2014 | Knightingale | A61F 13/505 604/385.15 |
| 8,894,626 | B2 * | 11/2014 | Beck | A61F 13/49003 604/385.15 |
| 9,301,887 | B2 * | 4/2016 | Coates | A61F 13/622 |
| 9,592,165 | B2 * | 3/2017 | Labit | A61F 13/505 |
| 2010/0318057 | A1 | 12/2010 | Yakem | |
| 2012/0116339 | A1 | 5/2012 | Labit et al. | |
| 2014/0257228 | A1 | 9/2014 | Wang et al. | |
| 2018/0193205 | A1 | 7/2018 | Beck | |

FOREIGN PATENT DOCUMENTS

| | | | |
|---|---|---|---|
| JP | 2016096883 | A | 5/2016 |
| JP | 2016154683 | A | 9/2016 |

OTHER PUBLICATIONS

International Preliminary Report on Patentability and Written Opinion of the International Searching Authority (Forms PCT/IB/326, PCT/IB/373 and PCT/ISA/237) issued on Sep. 7, 2023, by the International Bureau of WIPO, in corresponding International Application No. PCT/EP2021/054847. (7 pages).
Office Action issued on Oct. 28, 2024, by the Japanese Patent Office in corresponding Japanese Patent Application No. 2023-552089, and an English Translation of the Office Action. (9 pages).

* cited by examiner

REUSABLE OUTER SHELL FOR AN ABSORBENT INSERT

TECHNICAL FIELD

The present disclosure pertains to a reusable outer shell for an absorbent insert. In particular, this disclosure pertains to a reusable outer shell comprising a front pocket and a rear pocket for receiving the absorbent insert.

BACKGROUND OF THE INVENTION

The present disclosure generally relates to the field of reusable and washable diapers, and more particularly to a reusable outer shell adapted for receiving an absorbent insert, either a reusable absorbent insert or a disposable absorbent insert.

For economic and environmental reasons, parts of the absorbent article or the whole absorbent article may be washable and reusable. The absorbent article may for example include a washable outer shell which is intended to receive an absorbent insert which may be removably attached to the outer shell. The washable outer shell may be reused after soiling and removal of the absorbent insert by attaching a new absorbent insert to the outer shell. Attaching a new absorbent insert to the outer shell may be cumbersome, and a correct placement and attachment is important both for comfort and for leakage security of the absorbent article.

Disposable diapers, such as open diapers and pant-diapers, are generally provided with elasticized standing gather material along the leg openings and waist elastics in the front and rear portions along the absorbent insert outer edges, in order to prevent leakage. An absorbent article comprising a reusable outer shell and an absorbent insert may be more difficult to provide with elastics in direct connection with the absorbent insert. It is generally preferable to provide the outer shell with the elastic elements, since this may allow using absorbent inserts having a simpler construction resulting in less material consumption for the disposable parts.

Furthermore, washing of washable and reusable outer shells comprising hook materials for releasable fastening of the absorbent insert may lead to impaired functionality of hook material and undesired attachment of hook materials to other parts of the outer shell or to other items during washing. Undesired attachment of hook materials to other parts of the outer shell may have negative impact on the cleaning of the outer shell and attachment to other items washed together with the outer shell may damage fragile textile materials.

There is thus still a need for a reusable outer shell which has improved leakage security and comfort, and which also has prolonged life span. There is also a need for a reusable outer shell which is easy and convenient to wash and which has an improved washing result.

SUMMARY OF THE INVENTION

One or more of the above objects may be achieved with a washable outer shell in accordance with claim 1. Further embodiments are set out in the dependent claims and in the following description.

A reusable outer shell for a disposable absorbent insert according to the present disclosure comprises an inner surface intended to face the absorbent insert and an outer surface being opposite to the inner surface. The outer shell has an extension in the longitudinal direction and the transverse direction. The outer shell comprises a front region, a crotch region and a rear region, the outer shell comprising a front pocket in the front region and a rear pocket in the rear region. The front pocket is adapted to receive a front portion of the absorbent insert and the rear pocket is adapted to receive a rear portion of the absorbent insert, the front pocket having a front pocket transverse distal edge adapted to extend over the front portion of the absorbent insert and the rear pocket having a rear pocket transverse distal edge adapted to extend over the rear portion of the absorbent insert. The front pocket has a front pocket length, as measured along a longitudinal centerline of the outer shell from a front pocket transverse proximal edge to the front pocket transverse distal edge and the rear pocket has a rear pocket length, as measured along the longitudinal centerline of the outer shell and from a rear pocket transverse proximal edge to the rear pocket distal transverse edge, and wherein the rear pocket length is greater than the front pocket length.

The reusable outer shell is intended to be reused after soiling by removing of a soiled absorbent insert and by attaching a new absorbent insert to the reusable outer shell. Inserting a new absorbent insert to the outer shell may be cumbersome, and a correct placement and attachment is important both for comfort and for leakage security of the absorbent article. It has been found by the present inventors that by providing the outer shell with a front pocket arranged in the front region and a rear pocket arranged in the rear region the absorbent insert may be inserted into the outer shell and held in place both in the rear and front regions with a reduced risk of the absorbent insert being arranged obliquely in the outer shell with a resulting risk of side leakage.

It has furthermore been found by the present inventors that the absorbent insert was exerted to different types of stresses in the front region compared to in the rear region and that having a rear pocket with a greater length than a front pocket may provide the rear part of the absorbent insert with the stabilization needed to maintain a correct placement of the absorbent insert over the time of use.

Disposable diapers, such as open diapers and pant-diapers, are generally provided with elasticized standing gather material along the leg openings and waist elastics in the front and rear portions along the absorbent insert outer edges to prevent leakage. An absorbent article comprising two separate parts, as disclosed herein, may be more difficult to provide with elastics in direct connection with the absorbent insert. The provision of front and rear pockets to the outer shell according to the present disclosure were found to provide a protection from leakage in the front and rear regions since the pockets form front and rear leakage barriers.

The reusable outer shell is an outer shell that is capable of being reused multiple times by removing and replacing an absorbent insert with a new absorbent insert. The reusable outer shell may be a washable outer shell, capable of being washed without essential shrinkage or other damage, such as after five and up to forty washing occasions. The outer shell may made from a washable material such as a washable fabric. The outer shell may be made of one or more of the following materials: polyester, viscose, polyamide and/or cotton. The outer shell may be a stretchable outer shell, i.e., being made of a stretchable material. The outer shell may be an elastic shell, being elastic in the longitudinal and/or the transverse direction of the outer shell.

The rear pocket length may be at least 15% greater than the front pocket length, optionally at least 25% greater or at least 40% greater. This has been found to correspond to the increased stabilization needed in the rear portion of the absorbent insert and thereby provide a stable and reliable housing of the rear portion of the absorbent insert.

The rear pocket length may be 35 mm or more. Optionally, the rear pocket length may be from 35 mm to 100 mm. This has been found to provide a stable and reliable housing of the absorbent insert rear portion, providing leakage protection in the rear region of the outer shell, while not impairing the inlet properties of the absorbent insert.

The front pocket length may be 25 mm or more. Optionally, the front pocket length may be from 25 mm to 80 mm. This has been found to provide a stable and reliable housing of the absorbent insert front portion, while not impairing the inlet properties of the absorbent insert.

The rear pocket may have a rear pocket transverse distal edge region extending along the rear pocket transverse distal edge and an elastic member may be arranged in the rear pocket transverse distal edge region and extend in the transverse direction. This may facilitate a correct placement of the absorbent insert rear portion, in particularly over time. A further advantage is that the rear pocket transverse distal edge may rise with the elastic member arranged along the edge, thus enhancing the barrier function of the rear pocket.

The front pocket may have a front pocket transverse distal edge region extending along the front pocket transverse distal edge and an elastic member may be arranged in the front pocket transverse distal edge region and extend in the transverse direction. This may facilitate a correct placement of the absorbent insert front portion, in particularly over time. A further advantage is that the front pocket transverse distal edge may rise with the elastic member arranged along the edge, thus enhancing the barrier function of the front pocket.

The reusable outer shell may comprise a front hook member arranged on the inner surface of the outer shell, inside the front pocket, the front hook member having a length extending in the longitudinal direction and a width extending in the transverse direction. To provide the reusable outer shell with a front hook member, arranged inside the front pocket, has been found to enhance the retention and correct placement in the outer shell over time of the absorbent insert.

The reusable outer shell may comprise a rear hook member arranged on the inner surface of the outer shell inside the rear pocket, the rear hook member having a length extending in the longitudinal direction and a width extending in the transverse direction. To provide the reusable outer shell with a rear hook member, arranged inside the rear pocket, has been found to enhance the retention and correct placement in the outer shell over time of the absorbent insert.

The length of the rear hook member may be greater than the length of the front hook member. The present inventors have found that the rear portion of the absorbent insert is exerted to higher shear and pull forces than the front hook member, particularly when applying the absorbent insert, but also during use. The rear portion of the absorbent insert is for example both during day and night-time exerted to shear forces resulting from when the user walks, sits and changes position, and move around during sleep. It has therefore been found beneficial to have a rear hook member with a greater length compared to the front hook member for keeping the absorbent insert in place during use and particularly over a longer period.

The length of the rear hook member may be at least 15% greater than the length of the front hook member, optionally at least 25% greater or at least 40% greater.

The length of the rear hook member may be 10 mm or more, optionally within the range of from 10 mm to 70 mm. This has been found to provide a satisfying attachment of the absorbent insert rear portion and maintain a correct positioning of the absorbent insert in the outer shell during use.

The length of the front hook member may be 5 mm or more, optionally within the range of from 5 mm to 50 mm. This has been found to provide a satisfying attachment of the absorbent insert front portion.

The width of the rear hook member may be within the range of from 50 mm to 200 mm. Optionally the width of the rear hook member may be within the range of from 75 mm to 150 mm.

The width of the front hook member may be within the range of from 50 mm to 200 mm. Optionally the width of the front hook member may be within the range of from 75 mm to 150 mm.

The reusable outer shell may be washed after use, such as machine washed. However, washing of the outer shell may lead to impaired functionality of the front and rear hook members. During washing of the washable outer shell, threads and other material debris may get caught into the hook material and thereby deteriorate the ability of the hook member to attach to the absorbent insert backside. A further issue with the outer shell being provided with hook members is that during washing, undesired attachment of the hook materials to other parts of the outer shell or to other items during washing may have negative impact on the cleaning of the outer shell and may damage fragile textile materials washed together with the washable outer shell. However, since the front and rear hook members are provided in a respective front and rear pocket, the outer shell according to the present disclosure provides a protection of the hook members as such and for undesired attachment of the hook members during washing.

The rear hook member may comprise a first rear hook member part and a second rear hook member part, the first rear hook member part and the second rear hook member part being spaced apart from each other with a distance and arranged on a respective side of a longitudinal centerline of the outer shell, the width of the rear hook member being measured at the greatest width between an outermost transverse edges of the respective first rear hook member part and second rear hook member part and the length of the rear hook member being measured at the greatest length between a frontmost edge of the first rear hook member part and the second rear hook member part and a rearmost edge of the respective first rear hook member part and second rear hook member part. Such configuration may allow attachment of the absorbent insert at a respective rear corner portion while using less hook material and increasing the stiffness in the rear region of the outer shell. Since the first rear hook member part and the second rear hook member part are arranged on a respective side of the longitudinal centerline, folding of the outer shell along the centerline is made easier.

The first rear hook member part may have the same width as the second rear hook member part. The first rear hook member part may, alternatively or additionally, have the same length as the second rear hook member part.

The first rear hook member part and the second rear hook member part may cover from 25% to 100% of an area of the rear hook member, as measured by multiplying the length of the rear hook member with the width of the rear hook member.

The first rear hook member part and the second rear hook member part may cover from 35% to 80% of an area of the rear hook member.

The distance between the first rear hook member part and the second rear hook member part may correspond to from 15% to 75% of the width of the rear hook member, as measured at the greatest distance.

The front hook member may comprise a first front hook member part and a second front hook member part, the first front hook member part and the second front hook member part being spaced apart from each other with a distance and being arranged on a respective side of a longitudinal centerline of the outer shell, the width of the front hook member being measured at the greatest width between the outermost transverse edges of the respective first front hook member part and second front hook member part and the length of the front hook member being measured at the greatest length between a frontmost edge of the first front hook member part and the second front hook member part and a rearmost edge of the first front hook member part and second front hook member part, optionally wherein the first front hook member part has the same width and/or length as the second front hook member part. Such configuration may allow attachment of the absorbent insert at a respective front corner portion while using less hook material and reducing the stiffness in the front region of the outer shell. Since the first front hook member part and the second front hook member part are arranged on a respective side of the longitudinal centerline, folding of the outer shell along the centerline is made easier.

The distance between the first front hook member part and the second front hook member part may correspond to from 15% to 75% of the width of the front hook member, as measured at the greatest distance.

The first front hook member part and the second front hook member part may cover from 25% to 100% of an area of the front hook member, as measured by multiplying the length of the front hook member with the width of the front hook member.

The first front hook member part and the second front hook member part may cover from 35% to 80% of an area of the front hook member.

The rear hook member may have a width to length ratio of from 0.7:1 to 20:1. Optionally, the rear hook member may have a width to length ratio of from 1.1:1 to 15:1.

The front hook member may have a width to length ratio of from 1:1 to 40:1. Optionally, the front hook member may have a width to length ratio of from 1.5:1 to 40:1.

The outer shell in the rear region may comprise a first hook member provided in a first rear transverse corner region on an inner surface of the outer shell and a second hook member provided in a second rear transverse corner region of the outer shell, the outer shell may comprise a hook attachment zone on the outer surface in the front region of the outer shell, the first and second hook members being adapted to be attached to the hook attachment zone to form a waist opening.

The outer shell may comprise leg elastics arranged along a respective longitudinal side edge of the outer shell in the crotch region and waist elastics arranged along a rear transverse edge in the rear region of the outer shell.

BRIEF DESCRIPTION OF THE DRAWINGS

The present invention will be further explained hereinafter by means of non-limiting examples and with reference to the appended drawings wherein.

DETAILED DESCRIPTION

Figure 1A:
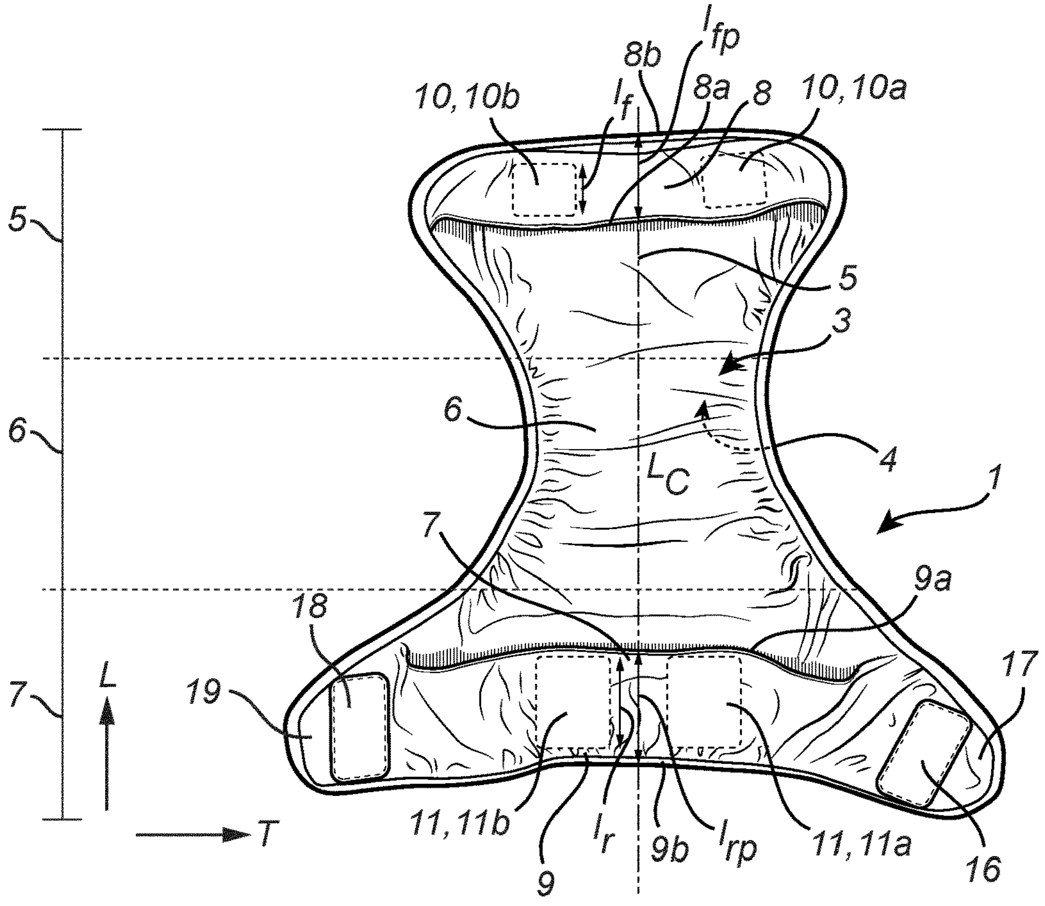
FIG. 1A illustrates a reusable outer shell according to the present disclosure as seen from the inner surface.

The invention will be described more closely below by reference to an exemplary embodiment. The invention may however be embodied in many different forms and should not be construed as limited to the embodiments set forth in the drawings and the description thereto.

Figure 1B:
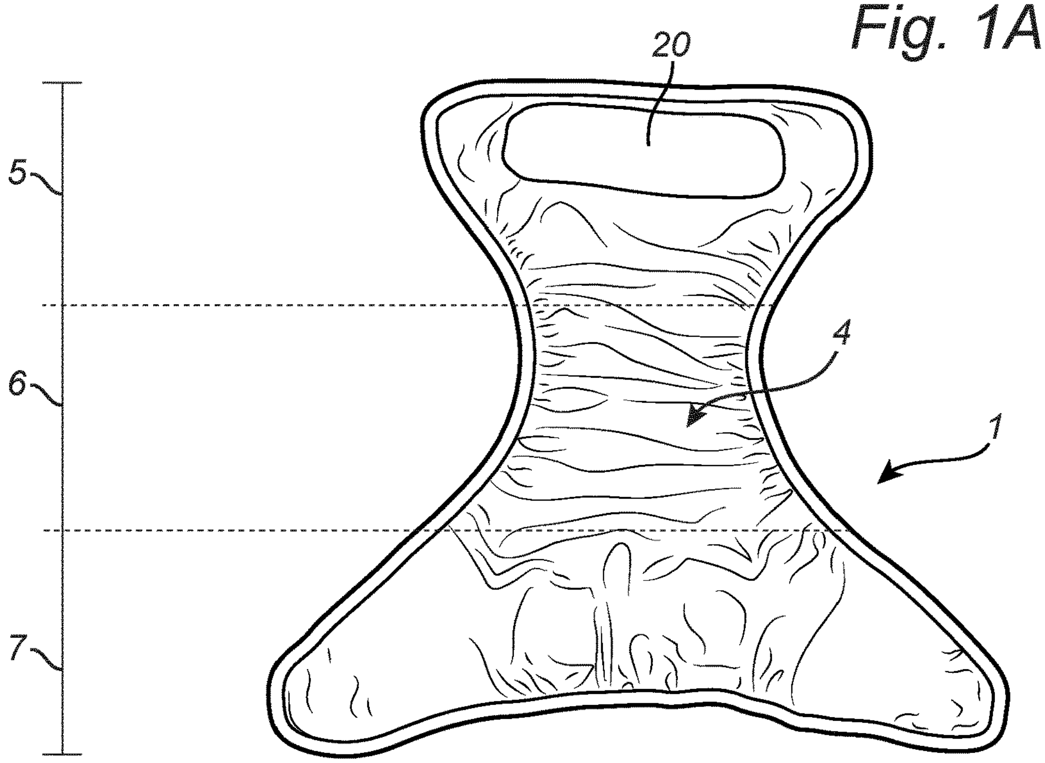
FIG. 1B illustrates the reusable outer shell from FIG. 1A as seen from the outer surface.

FIGS. 1A and 1B show a washable outer shell 1 according to the present disclosure. The outer shell 1 comprises an inner surface 3 and an outer surface 4 and has an extension in the longitudinal direction L and in the transverse direction T. FIG. 1A is an illustration of the washable cover 1 as seen from the inner surface 3 and FIG. 1B shows the outer shell 1 as seen from the outer surface 4. The outer shell 1 shown in FIGS. 1A and 1B is adapted to receive an absorbent insert 2 (shown in FIG. 3).

The reusable outer shell 1 is an outer shell that is capable of being reused multiple times. The reusable outer 1 shell may be a washable outer shell, capable of being washed without essential shrinkage or other damage. The outer shell 1 may be made from a washable material such as a washable fabric. The outer shell 1 may be made of one or more of the following materials; polyester, viscose, polyamide and/or cotton. The outer shell 1 may be a stretchable outer shell, i.e. being made of a stretchable material. The outer shell 1 may be an elastic shell, being elastic in the longitudinal direction L and/or the transverse direction T of the outer shell 1.

The outer shell 1 comprises a front region 5, a crotch region 6 and a rear region 7. The outer shell 1 comprises a front pocket 8 in the front region 5 and a rear pocket 9 in the rear region 7. The front pocket 8 has a front pocket length $l_{fp}$, as measured along a longitudinal centerline $L_c$ of the outer shell 1 from a front pocket transverse proximal edge 8*b* to the front pocket transverse distal edge 8*a* and the rear pocket 9 has a rear pocket length $l_{rp}$, as measured along the longitudinal centerline $L_c$ of the outer shell 1 and from a rear pocket transverse proximal edge 9*b* to the inner rear transverse edge 9*a*. The rear pocket length $l_{rp}$ is greater than the front pocket length $l_{fp}$. The rear pocket length $l_{rp}$ may be at least 15% greater than the front pocket length $l_{fp}$. The rear pocket length $l_{rp}$ may be 35 mm or more and the front pocket length $l_{fp}$ may be 25 mm or more.

The front pocket 8 and the rear pocket 9 may constitute of the same or different type of material as the outer shell 1. The pocket material may, as well as the outer shell material, be capable of being washed several times without essential shrinkage or other damage. The pockets may be made from a washable material such as a washable fabric. The pocket material may be a polyester, polyamid, cotton and/or a viscose material. The pocket material may be made of a stretchable material. The pocket material may be an elastic material, being elastic in the longitudinal direction L and/or the transverse direction T.

A front hook member 10 is arranged on the inner surface 3 of the outer shell 1, inside the front pocket 8 and a rear hook member 11 is arranged on the inner surface 3 of the outer shell 1 inside the rear pocket 9. The rear hook member 11 comprises a first rear hook member part 11*a* and a second rear hook member part 11*b*. The front hook member 10 comprises a first front hook member part 10*a* and a second front hook member part 10*b*. The first front hook member part 10*a* and the second front hook member part 10*b* are spaced apart from each other and are arranged on a respective side of a longitudinal centerline $L_c$ of the outer shell 1. The first rear hook member part 11*a* and the second rear hook member part 11*b* are spaced apart from each other and are arranged on a respective side of a longitudinal centerline $L_c$ of the outer shell 1. The front hook member has a length $l_f$ and the rear hook member has a length $l_r$, the respective lengths each extending in the longitudinal direction L. The length $l_r$ of the rear hook member 11 is greater than the length $l_f$ of the front hook member 10.

The front and rear hook members 10,11 may comprise any hook-type material with a hook surface structure and the terms hook members are to be interpreted as encompassing the hook part of a hook and loop fastening system, e.g., known as a VELCRO® system. The "hooks" may have many different shapes which are adapted to engage with a loop part of the hook and loop fastening system. The hooks may, purely as an example, by of a J-shape, mushroom shape, and palm tree shape.

The outer shell 1 comprises a first hook member 16 in the rear region 7 provided in a first rear transverse corner region 17 on the rear pocket 9 and a second hook member 18 provided in a second rear transverse corner region 19 on the rear pocket, depending on the transverse extension of the pocket 9, the first and second hook members 16,18 may be provided on the rear pocket 9 or on the inner surface 3 of the outer shell 1.

The outer shell 1 comprises a hook attachment zone 20 on the outer surface 4 in the front region 5 of the outer shell 1, as illustrated in FIG. 1B. The first and second hook members 16,18 are adapted to be attached to the hook attachment zone 20 to form a waist opening.

The first and second hook members 16,18 may comprise any hook-type material with a hook surface structure and the hook attachment zone 20 may comprise any loop surface structure, and the terms hook members are to be interpreted as encompassing the hook part of a hook and loop fastening system, e.g., known as a VELCRO® system. The "hooks" may have many different shapes which are adapted to engage with a loop part of the hook and loop fastening system. The hooks may, purely as an example, by of a J-shape, mushroom shape, and palm tree shape. The hook attachment zone 20 may comprise any type of loop surface structure, which is here to be understood to encompass a surface structure to which a hook material of a hook and loop fastening system is attachable. Accordingly, a loop surface structure may include fibers or threads extending from a surface and back into the surface to define genuine icons, as we as a surface structure including fibers or threads extending out from a surface and having loose ends, which fibers or threads entangle with each other. Upon attachment of the respective hook members 16, 18, the hook surface structure engages with the loop surface structure providing a releasable attachment between the elements.

The outer shell 1 comprises leg elastics 22,23 arranged along a respective longitudinal side edge of the outer shell 1 in the crotch region 6 and waist elastics 24 arranged along a rear transverse edge in the rear region 7 of the outer shell 1.

Figure 2:
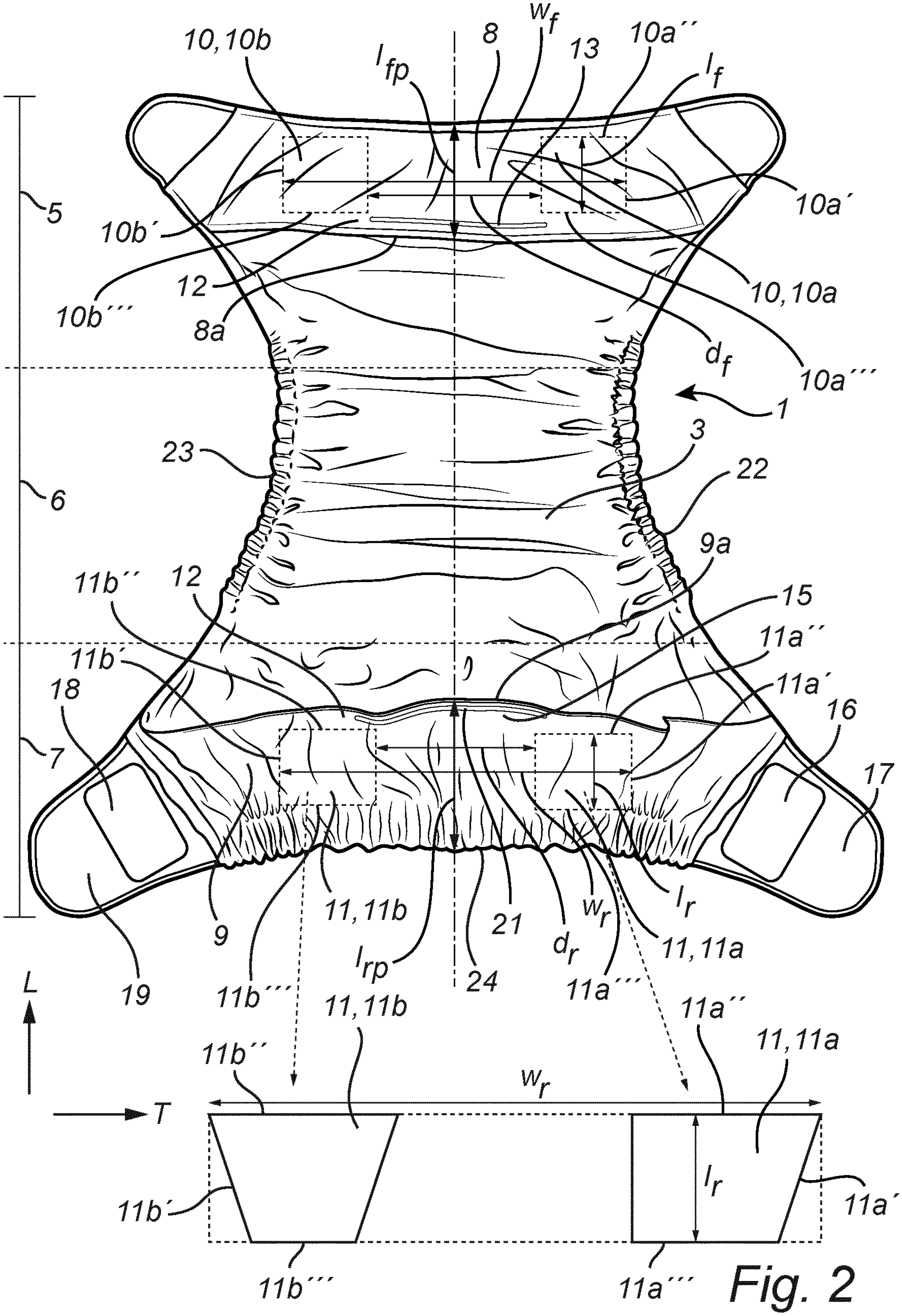
FIG. 2 illustrates a reusable outer shell according to the present disclosure as seen from the inner surface; and, FIG. 3 illustrates the reusable outer shell according to FIG. 2 comprising an absorbent insert.

FIG. 2 illustrates a washable outer shell 1 according to the present disclosure. The outer shell 1 is illustrated as seen from an inner surface 3 and has an extension in the longitudinal direction L and in the transverse direction T. The outer shell 1 comprises a front region 5, a crotch region 6 and a rear region 7. The outer shell 1 comprises a front pocket 8 in the front region 5 and a rear pocket 9 in the rear region 7. The front pocket 8 has a front pocket length $l_{fp}$, as measured along a longitudinal centerline $L_c$ of the outer shell 1 from a front pocket transverse proximal edge 8*b* to the front pocket transverse distal edge 8*a* and the rear pocket has a rear pocket length $l_{rp}$, as measured along the longitudinal centerline $L_c$ of the outer shell 1 and from a rear pocket transverse proximal edge 9*b* to the inner rear transverse edge 9*a*. The rear pocket length $l_{rp}$ is greater than the front pocket length $l_{fp}$. The rear pocket length $l_{rp}$ may be at least 15% greater than the front pocket length $l_{fp}$ The rear pocket length $l_{rp}$ may be 35 mm or more and the front pocket length ($l_{fp}$) may be 25 mm or more.

A front hook member 10 is arranged on the inner surface 3 of the outer shell 1, inside the front pocket 8 and a rear hook member 11 is arranged on the inner surface 3 of the outer shell 1 inside the rear pocket 9. The rear hook member 11 comprises a first rear hook member part 11*a* and a second rear hook member part 11*b*. The front hook member 10 comprises a first front hook member part 10*a* and a second front hook member part 10*b*. The first front hook member part 10*a* and the second front hook member part 10*b* are spaced apart from each other with a distance d f and are arranged on a respective side of a longitudinal centerline $L_c$ of the outer shell 1. The first rear hook member part 11*a* and the second rear hook member part 11*b* are arranged on a respective side of a longitudinal centerline $L_c$ of the outer shell 1.

The front hook member 10 has a length $l_f$ extending in the longitudinal direction L and a width w f extending in the transverse direction T. The length $l_f$ is measured at the greatest length, in the longitudinal direction L, between a frontmost edge 10*a*",10*b*" of the first front hook member part 10*a* and the second front hook member part 10*b* and a rearmost edge 10*a*''',10*b*''' of the first front hook member part 10*a* and second front hook member part 10*b*.

The rear hook member 11 has a length $l_r$ extending in the longitudinal direction L and a width $w_f$ extending in the transverse direction T. The length $l_r$ is measured at the greatest length, in the longitudinal direction L, between a frontmost edge 11*a*",11*b*" of the first rear hook member part 11*a* and the second rear hook member part 11*b* and a rearmost edge 11*a*''',11*b*''' of the first rear hook member part 11*a* and second rear hook member part 11*b*.

The length $l_r$ of the rear hook member 11 is greater than the length $l_f$ of the front hook member 10.

The length of the of the front hook member 10 may be the same over at least 50% of the front hook member 10, as seen in the transverse direction T and the length of the of the rear hook member 11 may be the same over at least 50% of the rear hook member 11, as seen in the transverse direction T.

As for the measurements of the lengths of the hook members, the width $w_r$ of the rear hook member 11 is measured, in the transverse direction T, at the greatest width between an outermost transverse edges 11*a*',11*b*' of the respective first rear hook member part 11*a* and second rear hook member part 11*b*. An alternative hook configuration is illustrated in FIG. 2 below the outer shell 1, wherein the first and second rear hook member parts 11*a*,11*b* each has a rhombus shape. The width $w_r$ of the rear hook member 11 is thus not constant, as seen in the longitudinal direction L. The width $w_r$ of the rear hook member 11 is measured by drawing an extension in the longitudinal direction L, at the outermost section of the respective outermost transverse edges 11*a*',11*b*' and measuring the width therebetween.

The first front hook member part 10*a* and the second front hook member part 10*b* cover from 25% to 100% of an area of the front hook member 10, as measured by multiplying the length $l_f$ of the front hook member 10 with the width $w_f$ of the front hook member 10.

The first rear hook member part 11*a* and the second rear hook member part 11*b* cover from 25% to 100% of an area of the rear hook member 11, as measured by multiplying the length $l_r$ of the rear hook member 11 with the width $w_r$ of the rear hook member 11.

In FIG. 2, the first and the second front hook member parts have the same widths and the same length and are arranged with a distance d f corresponding to from 15% to 75% of the width $w_f$ of the front hook member 10, such as from 40% to 60% of the width $w_f$ of the front hook member 10.

The front pocket 8 has a front pocket transverse distal edge region 12 extending along the front pocket transverse distal edge 8*a* and an elastic member 13 is arranged in the front pocket transverse distal edge region 12 and extends in the transverse direction T.

The rear pocket 9 has a rear pocket transverse distal edge region 15 extending along the rear pocket transverse distal edge 9*a* and an elastic member 21 is arranged in the rear pocket transverse distal edge region 15 and extends in the transverse direction T.

The elastic members 13,21 may be any suitable type of elastic members, such as for example a respective elastic thread, foam elastics or strips of an elastic film. The elastic members 13,21, may be of the same type of elastic material or of different types of elastic materials.

The rear region 7 of the outer shell 1 furthermore comprises a first corner region 17 and a second corner region 19. The outer shell 1 comprises a first hook member 16 provided in the first corner region 17 and a second hook member 18 provided in the second corner region 19 on an inner side of the outer shell 1. The first and the second hook members 16,18 are intended to be attached to a hook attachment zone 20 (shown in FIG. 1B) provided on the outer surface 4 of the outer shell 1 to form a waist opening.

Figure 3:
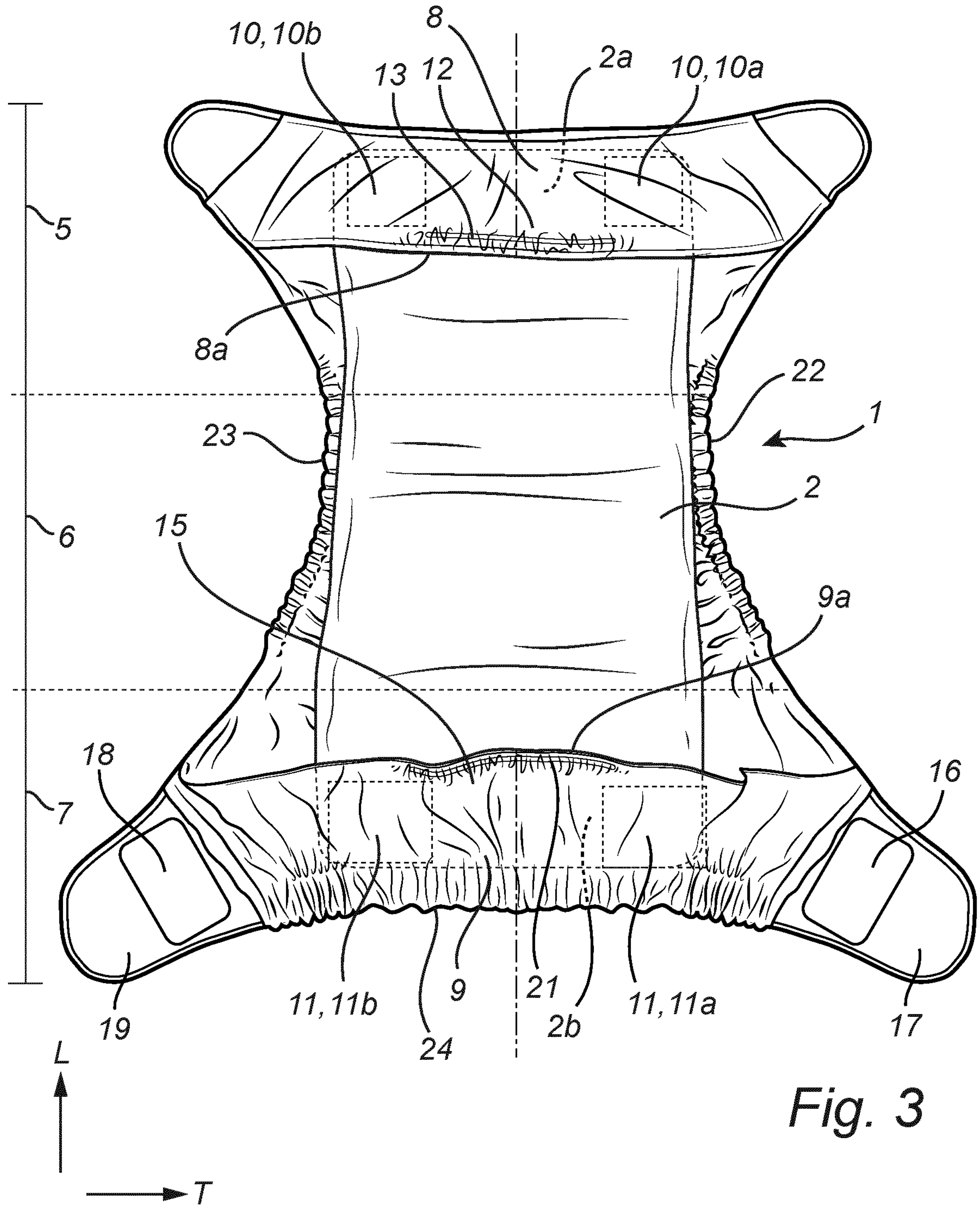

FIG. 3 illustrates an outer shell 1 according to the present disclosure provided with an absorbent insert 2. The outer shell 1 comprises a front pocket 8 arranged in a front region 5 of the outer shell 1 on the inner surface 3 thereof and a rear pocket 9 arranged on the inner surface 3 of the outer shell in a rear region 7 thereof. The front pocket 8 receives a front section 2*a* of the absorbent insert 2 and the rear pocket 9 receives a rear section 2*b* of the absorbent insert 2.

The front pocket 8 comprises a front pocket elastic member 13 arranged in a front pocket transverse distal edge region 12 extending along the front pocket transverse distal edge 8*a* and the rear pocket 9 comprises a rear pocket elastic member 21 arranged in a rear pocket transverse distal edge region 15 extending along the rear pocket transverse distal edge 9*a*.

To releasably attach the absorbent insert 2 to the outer shell 1, the outer shell 1 comprises a front hook member 10 arranged in the front pocket 8 of the outer shell 1 and a rear hook member 11 arranged in the rear pocket 9 of the outer shell 1. The front and rear hook members 10,11 are releasably attached to a backsheet of the absorbent insert (not shown), such as for example a nonwoven/film layer backsheet. The front and rear hook members 10,11 may alternatively be attached to a loop material zone provided on the backsheet of the absorbent insert 2.

The front hook member 10 comprises a first front hook member part 10*a* and a second front hook member part 10*b* and the rear hook member 11 comprises a first rear hook member part 11*a* and a second rear hook member part 11*b*.

The outer shell 1 is of the open diaper type. The rear region 7 of the outer shell 1 furthermore comprises a first corner region 17 and a second corner region 19. The outer shell 1 comprises a first hook member 16 provided in the first corner region 17 and a second hook member 18 provided in the second corner region 19. The first and the second hook members 16,18 are intended to be arranged to face the outer surface 4 of the outer shell 1 during use and to be attached to a hook attachment zone 20 (shown in FIG. 1B) provided on the outer surface 4 of the outer shell 1 to form a waist opening.

The outer shell 1 comprises leg elastics 22,23 arranged along a respective longitudinal side edge of the outer shell 1 in the crotch region 6 and waist elastics 24 arranged along a rear transverse edge in the rear region 7 of the outer shell 1.

The invention claimed is:

1. A reusable outer shell for a disposable absorbent insert, the outer shell comprising:
- an inner surface intended to face the absorbent insert and an outer surface being opposite to the inner surface,
- the outer shell having an extension in the longitudinal direction and the transverse direction,
- the outer shell comprising a front region, a crotch region and a rear region,
- the outer shell comprises a front pocket cover forming a front pocket in the front region and a rear pocket cover forming a rear pocket in the rear region,
- wherein the front pocket cover has a front pocket transverse distal edge region extending along a front pocket transverse distal edge, and an elastic member is arranged in the front pocket transverse distal edge region and extends in the transverse direction for less than an entirety of the front pocket transverse distal edge,
- wherein the rear pocket cover has a rear pocket transverse distal edge region extending along a rear pocket transverse distal edge, and an elastic member is arranged in the rear pocket transverse distal edge region and extends in the transverse direction for less than an entirety of the rear pocket transverse distal edge,
- the front pocket being adapted to receive a front portion of the absorbent insert and the rear pocket being adapted to receive a rear portion of the absorbent insert,
- the front pocket having a front pocket transverse distal edge adapted to extend over the front portion of the absorbent insert and the rear pocket having a rear pocket transverse distal edge adapted to extend over the rear portion of the absorbent insert,
- the front pocket has a front pocket length, as measured along a longitudinal centerline of the outer shell from a front pocket transverse proximal edge to the front pocket transverse distal edge and the rear pocket has a rear pocket length, as measured along the longitudinal centerline of the outer shell and from a rear pocket transverse proximal edge to the rear pocket transverse distal edge, and
- wherein the rear pocket length is greater than the front pocket length.

2. The reusable outer shell according to claim 1, wherein the rear pocket length is at least 15% greater than the front pocket length.

3. The reusable outer shell according to claim 1, wherein the reusable outer shell comprises a front hook member arranged on the inner surface of the outer shell, inside the front pocket and a rear hook member arranged on the inner surface of the outer shell inside the rear pocket, wherein the front hook member has a length extending in the longitudinal direction and a width extending in the transverse direction and the rear hook member has a length extending in the longitudinal direction and a width extending in the transverse direction.

4. The reusable outer shell according to claim 3, wherein the length of the rear hook member is greater than the length of the front hook member.

5. The reusable outer shell according to claim 3, wherein the length of the rear hook member is at least 15% greater than the length of the front hook member.

6. The reusable outer shell according to claim 3, wherein the width of the rear hook member is within the range of from 50 mm to 200 mm.

7. The reusable outer shell according to claim 3, wherein the width of the front hook member is within the range of from 50 mm to 200 mm.

8. The reusable outer shell according to claim 3, wherein the rear hook member comprises a first rear hook member part and a second rear hook member part, the first rear hook member part and the second rear hook member part being spaced apart from each other with a distance and arranged on a respective side of a longitudinal centerline of the outer shell, the width of the rear hook member being measured at the greatest width between an outermost transverse edges of the respective first rear hook member part and second rear hook member part and the length of the rear hook member being measured at the greatest length between a frontmost edge of the first rear hook member part or the second rear hook member part and a rearmost edge of the respective first rear hook member part or second rear hook member part, optionally wherein the first rear hook member part has the same width and/or length as the second rear hook member part.

9. The reusable outer shell according to claim 8, wherein the first rear hook member part and the second rear hook member part cover from 25% to 100% of an area of the rear hook member, as measured by multiplying the length of the rear hook member with the width of the rear hook member.

10. The reusable outer shell according to claim 8, wherein the distance between the first rear hook member part and the second rear hook member part corresponds to from 15% to 75% of the width of the rear hook member.

11. The reusable outer shell according to claim 3, wherein the front hook member comprises a first front hook member part and a second front hook member part, the first front hook member part and the second front hook member part being spaced apart from each other with a distance and being arranged on a respective side of a longitudinal centerline of the outer shell, the width of the front hook member being measured at the greatest width between the outermost transverse edges of the respective first front hook member part and second front hook member part and the length of the front hook member being measured at the greatest length between a frontmost edge of the first rear hook member part or the second rear hook member part and a rearmost edge of the first front hook member part and second front hook member part, optionally wherein the first front hook member part has the same width and/or length as the second front hook member part.

12. The reusable outer shell according to claim 11, wherein the distance between the first front hook member part and the second front hook member part corresponds to from 15% to 75% of the width of the front hook member.

13. The reusable outer shell according to claim 11, wherein the first front hook member part and the second front hook member part cover from 25% to 100% of an area of the front hook member, as measured by multiplying the length of the front hook member with the width of the front hook member.

14. The reusable outer shell according to claim 3, wherein the rear hook member has a width to length ratio within the range of from 0.7:1 to 20:1.

15. The reusable outer shell according to claim 3, wherein the front hook member has a width to length ratio of from 1:1 to 40:1.

16. The reusable outer shell according to claim 1, wherein the outer shell in the rear region comprises a first hook member provided in a first rear transverse corner region on an inner surface of the outer shell and a second hook member is provided in a second rear transverse corner region on the inner surface of the outer shell, the outer shell comprises a hook attachment zone on the outer surface in the front region of the outer shell, the first and second hook members being adapted to be attached to the hook attachment zone to form a waist opening.

* * * * *